(12) United States Patent
Calienni et al.

(10) Patent No.: US 9,193,732 B2
(45) Date of Patent: Nov. 24, 2015

(54) SALT(S) OF 7-CYCLOPENTYL-2-(5-PIPERAZIN-1-YL-PYRIDIN-2-YLAMINO)-7H-PYRROLO[2,3-D]PYRIMIDINE-6-CARBOXYLIC ACID DIMETHYLAMIDE AND PROCESSES OF MAKING THEREOF

(75) Inventors: John Vincent Calienni, Cranford, NJ (US); Guang-Pei Chen, Livingston, NJ (US); Baoqing Gong, Morris Plains, NJ (US); Prasad Koteswara Kapa, Parsippany, NJ (US); Vishal Saxena, Quincy, MA (US)

(73) Assignees: Novartis AG, Basel (CH); Astex Therapeutics, LTD, Cambridge (GB)

( * ) Notice: Subject to any disclaimer, the term of this patent is extended or adjusted under 35 U.S.C. 154(b) by 0 days.

(21) Appl. No.: 13/882,353

(22) PCT Filed: Nov. 9, 2011

(86) PCT No.: PCT/US2011/059890
§ 371 (c)(1),
(2), (4) Date: Apr. 29, 2013

(87) PCT Pub. No.: WO2012/064805
PCT Pub. Date: May 18, 2012

(65) Prior Publication Data
US 2013/0217698 A1    Aug. 22, 2013

Related U.S. Application Data

(60) Provisional application No. 61/412,064, filed on Nov. 10, 2010.

(51) Int. Cl.
| | | |
|---|---|---|
| C07D 487/04 | (2006.01) |
| A61K 31/519 | (2006.01) |
| A61P 35/00 | (2006.01) |
| C07D 401/12 | (2006.01) |
| C07C 55/10 | (2006.01) |
| C07D 213/74 | (2006.01) |
| C07D 213/73 | (2006.01) |

(52) U.S. Cl.
CPC .............. *C07D 487/04* (2013.01); *C07C 55/10* (2013.01); *C07D 213/73* (2013.01); *C07D 213/74* (2013.01); *C07D 401/12* (2013.01)

(58) Field of Classification Search
CPC ............................ C07D 487/04; A61K 31/519
USPC ........... 514/252.18, 252.16, 253.01; 544/280, 544/360, 364
See application file for complete search history.

(56) References Cited

U.S. PATENT DOCUMENTS

| 8,415,355 B2 * | 4/2013 | Brain et al. ............... 514/252.16 |
| 8,685,980 B2 * | 4/2014 | Besong et al. ........... 514/252.16 |
| 2014/0135312 A1 * | 5/2014 | Besong et al. ........... 514/210.21 |

FOREIGN PATENT DOCUMENTS

| WO | 0147507 | 7/2001 |
| WO | 2005023761 | 3/2005 |
| WO | 2006/008545 | 1/2006 |
| WO | 2007014022 | 2/2007 |
| WO | 2007/075783 | 7/2007 |
| WO | 2010/020675 | 2/2010 |
| WO | 2011/133888 A1 | 10/2011 |
| WO | 2012064805 | 5/2012 |

OTHER PUBLICATIONS

U.S. Appl. No. 14/307,901, filed Jun. 18, 2014.*
Marcos Malumbres et al., "CDK inhibitors in cancer therapy: what is next?", Trends in Pharmacological Sciences, vol. 29, No. 1, pp. 16-21, 2008.
Serajuddin, 2007, Advanced Drug Delivery Reviews 59:603-616.
Stahl et al. eds., 2008, Handbook of pharmaceutical salts. Properties, selection and use (Wiley-VCH), pp. 265-327.
Bastin et al., 2000, (Organic Process Research & Development, 4:427-435).
Berge et al., "Pharmaceutical Salts", Journal of Pharmaceutical Sciences, vol. 66, Issue 1, pp. 1-19, 1977.
Ashizawa et al., "Science of Polymorphism Phenomena and Crystallization of Pharmaceutical Products", published by Maruzen Planet Co., Ltd., 2002, pp. 305-311.

* cited by examiner

*Primary Examiner* — Sreeni Padmanabhan
*Assistant Examiner* — Irina Neagu
(74) *Attorney, Agent, or Firm* — Jennifer Chapman

(57) ABSTRACT

This invention relates to (1) process of making 7-Cyclopentyl-2-(5-piperazin-1-yl-pyridin-2-ylamino)-7H-pyrrolo[2,3-d]pyrimidine-6-carboxylic acid dimethylamide and salts thereof; (2) novel salt(s) of 7-Cyclopentyl-2-(5-piperazin-1-yl-pyridin-2-ylamino)-7H-pyrrolo[2,3-d]pyrimidine-6-carboxylic acid dimethylamide; (3) pharmaceutical compositions comprising the same; and (4) methods of treatment using the same.

9 Claims, 6 Drawing Sheets

SALT(S) OF 7-CYCLOPENTYL-2-(5-PIPERAZIN-1-YL-PYRIDIN-2-YLAMINO)-7H-PYRROLO[2,3-D]PYRIMIDINE-6-CARBOXYLIC ACID DIMETHYLAMIDE AND PROCESSES OF MAKING THEREOF

The instant application is a National Stage entry of PCT/US11/59890, filed on Nov. 9, 2011, claiming priority from U.S. Provisional Patent Application No. 61/412,064 filed on Nov. 20, 2010.

FIELD OF THE INVENTION

This invention relates to (1) process of making 7-Cyclopentyl-2-(5-piperazin-1-yl-pyridin-2-ylamino)-7H-pyrrolo[2,3-d]pyrimidine-6-carboxylic acid dimethylamide and salt(s) thereof; (2) novel salt(s) of 7-Cyclopentyl-2-(5-piperazin-1-yl-pyridin-2-ylamino)-7H-pyrrolo[2,3-d]pyrimidine-6-carboxylic acid dimethylamide; (3) pharmaceutical compositions comprising the same; and (4) methods of treatment using the same.

RELATED BACKGROUND ART

The compound 7-Cyclopentyl-2-(5-piperazin-1-yl-pyridin-2-ylamino)-7H-pyrrolo[2,3-d]pyrimidine-6-carboxylic acid dimethylamide of Formula (I)

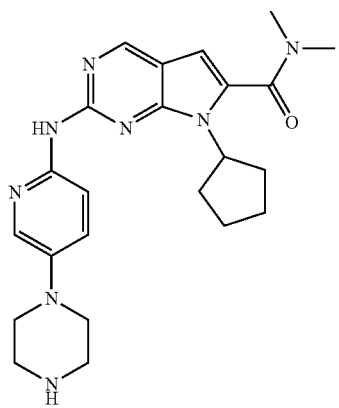

(I)

and its synthesis is specifically described in WO 2010/020675 A1, Example 74. WO2010/020675 discloses that compound of Formula (I) has valuable pharmacological properties and can be used, for example, (1) as inhibitors of cyclin dependent kinases, (in particular, cyclin dependent kinases selected from CDK1, CDK2, CDK3, CDK4, CDK5, CDK6 and CDK9); and (2) as modulators and/or inhibitors of glycogen synthase kinase-3 (GSK-3).

WO2010/020675 does not disclose or suggest the succinate salt of 7-Cyclopentyl-2-(5-piperazin-1-yl-pyridin-2-ylamino)-7H-pyrrolo[2,3-d]pyrimidine-6-carboxylic acid dimethylamide.

SUMMARY OF THE INVENTION

The present invention is directed to succinate salt of 7-Cyclopentyl-2-(5-piperazin-1-yl-pyridin-2-ylamino)-7H-pyrrolo[2,3-d]pyrimidine-6-carboxylic acid dimethylamide.

The succinate salt is described by Formula (II):

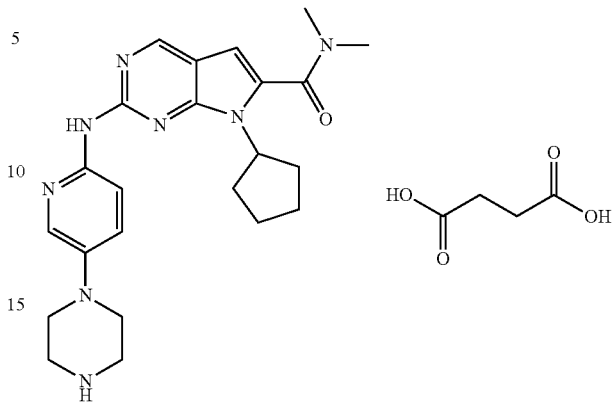

(II)

The present invention is also directed to a method of preparing the compound of Formula (II).

The present invention is further directed to a method of preparing the compound of Formula (I).

The present invention is yet further directed to a method of preparing the compound of Formula (III)

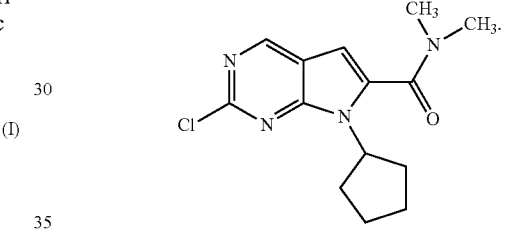

(III)

The present invention is also further directed a method of preparing the compound of Formula (IV):

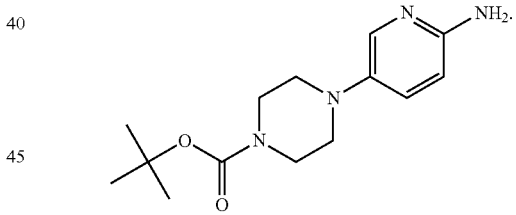

(IV)

The present invention is further directed to pharmaceutical compositions comprising the salt of Formula (II) and at least one pharmaceutically acceptable carrier, diluent, vehicle or excipient.

The present invention is also directed to a method of treating a disease which responds to an inhibition of cyclin dependent kinases, (in particular, cyclin dependent kinases selected from CDK1, CDK2, CDK3, CDK4, CDK5, CDK6 and CDK9) comprising the step of administering to a subject in need of such treatment a therapeutically effective amount of the compound of Formula (II).

DETAILED DESCRIPTION OF THE INVENTION

Figure 1:
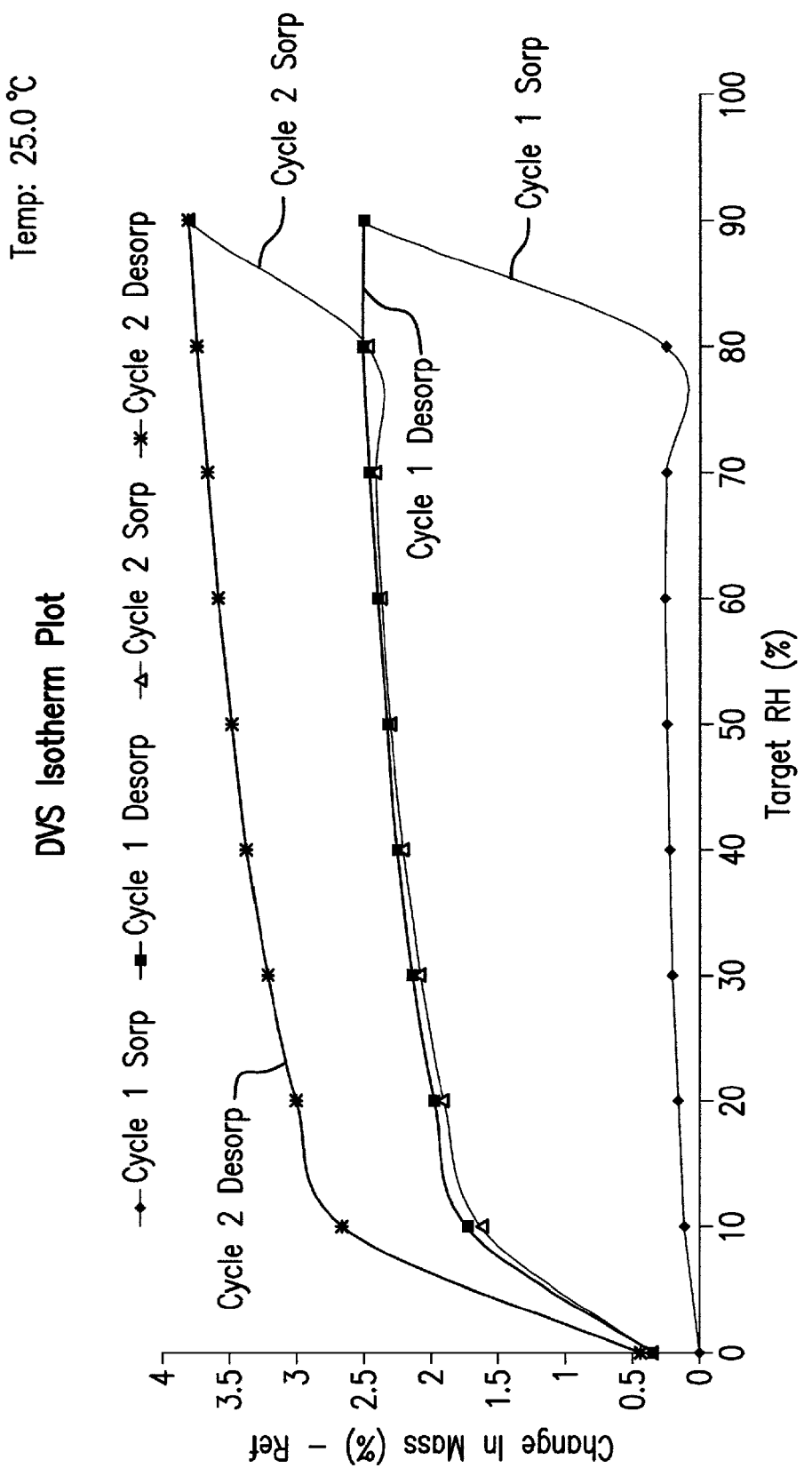
FIG. 1 shows Dynamic Vapor Sorption (DVS) isotherm plot of Compound of Formula (II) (0-90-0% Relative Humidity (RH) Cycle).

The present invention is directed to succinate salt of 7-Cyclopentyl-2-(5-piperazin-1-yl-pyridin-2-ylamino)-7H-pyrrolo[2,3-d]pyrimidine-6-carboxylic acid dimethylamide.

The succinate salt is described by Formula (II):

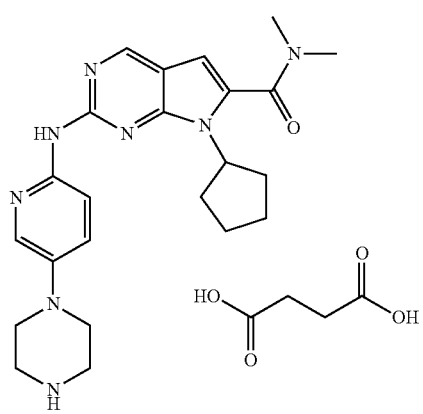

(II)

The succinate salt of 7-Cyclopentyl-2-(5-piperazin-1-yl-pyridin-2-ylamino)-7H-pyrrolo[2,3-d]pyrimidine-6-carboxylic acid dimethylamide can be either in non-hydrate, hydrate forms, or mixtures thereof.

In one embodiment, the succinate salt is greater than 99.9% in the form of non-hydrate.

In one embodiment, the succinate salt is greater than 99% in the form of non-hydrate.

In one embodiment, the succinate salt is greater than 97% in the form of non-hydrate.

In one embodiment, the succinate salt is greater than 95% in the form of non-hydrate.

In one embodiment, the succinate salt is greater than 90% in the form of non-hydrate.

The non-hydrate form of succinate salt of 7-Cyclopentyl-2-(5-piperazin-1-yl-pyridin-2-ylamino)-7H-pyrrolo[2,3-d]pyrimidine-6-carboxylic acid dimethylamide has good stability, non-hygroscopicity, and good solubility.

The present invention is also directed to a method of preparing the compound of Formula (I) and the compound of Formula (II):

Process Scheme for Making Compound of Formula (I) and Compound of Formula (II)

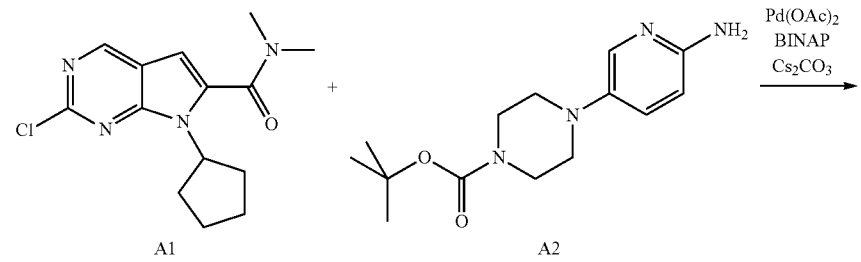

A1              A2

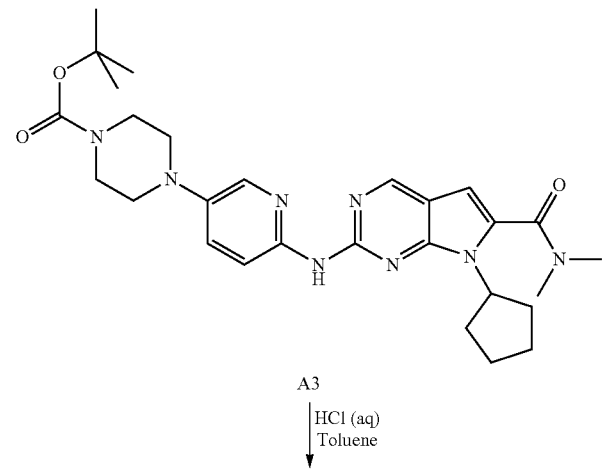

A3

HCl (aq)
Toluene

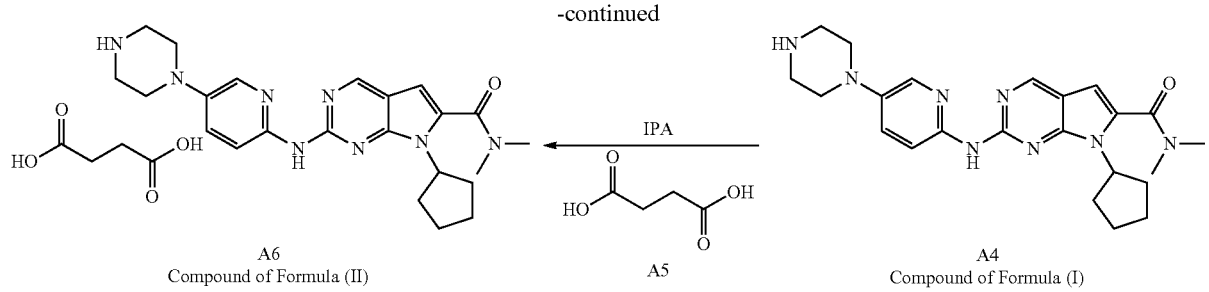

The present invention is further directed to a method of preparing the compound of Formula (III):

Process Scheme for Making Compound of Formula (III)

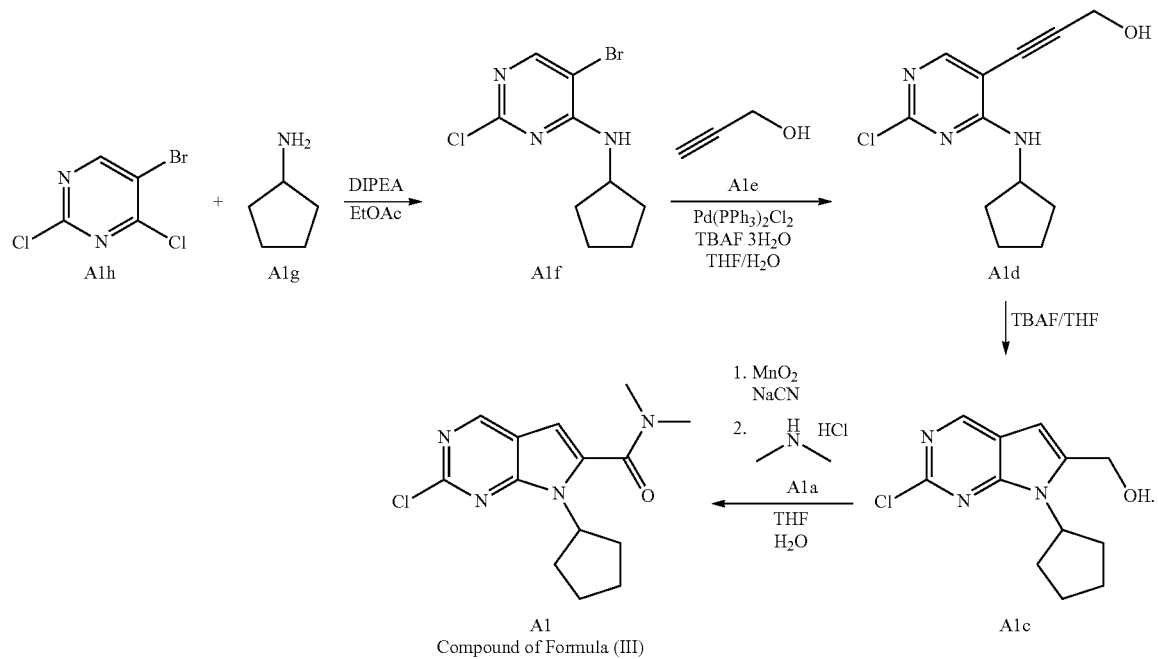

Compare to previous method of making the Compound of Formula (III), the present process improved the overall yield of the compound Formula (III) (i.e., A1) from 4% to 30%. In addition, the five column purification steps required by the previous method are not needed in this improved process.

The present invention is also further directed a method of preparing the compound of Formula (IV):

Process Scheme for Making Compound of Formula (IV)

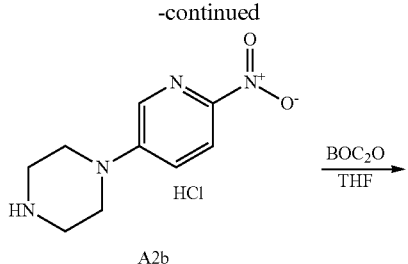

-continued

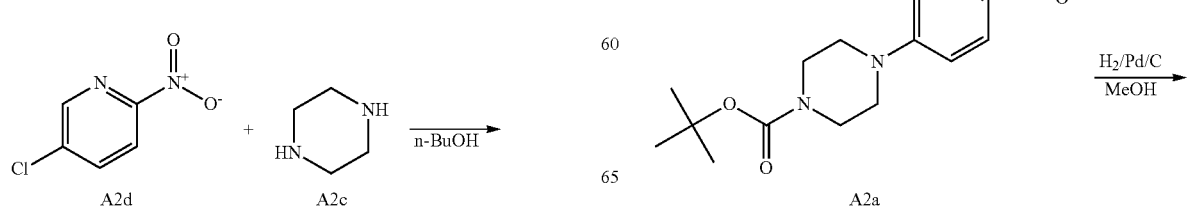

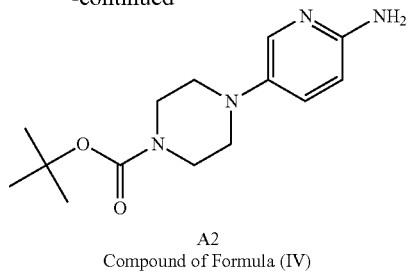

A2
Compound of Formula (IV)

In the present synthesis of Compound of Formula (IV) (i.e., A2), a facile method is developed for replacing the chloride in A2d with A2c using n-butanol as a solvent. This process increases the yield and avoided chromatographic purification of the Compound of Formula (IV) for further processes.

In summary, a scalable, safer, simpler, higher yielding, and more cost efficient process for manufacturing starting materials A1 (Compound of Formula (III)), A2 (Compound of Formula (IV)), free base A4 (Compound of Formula (I)), and succinate salt A6 (Compound of Formula (II)) is developed. Compare to previous synthesis processes, the overall procedure shortened the synthetic steps and increased the overall yield from 0.9% to 12%.

The present invention is further directed to pharmaceutical compositions comprising the salt of Formula (II) and at least one pharmaceutically acceptable carrier, diluent, vehicle or excipient.

The present invention is also directed to a method of treating a disease which responds to an inhibition of cyclin dependent kinases, (in particular, cyclin dependent kinases selected from CDK1, CDK2, CDK3, CDK4, CDK5, CDK6 and CDK9) comprising the step of administering to a subject in need of such treatment a therapeutically effective amount of the compound of Formula (II).

Such disease which responds to an inhibition of cyclin dependent kinases include, but not limited to breast cancer, genitourinary cancer, lung cancer, gastrointestinal cancer, epidermoid cancer, melanoma, ovarian cancer, pancreas cancer, neuroblastoma, head and/or neck cancer or bladder cancer, or in a broader sense renal, brain or gastric cancer; leukemias, hyperplasias, stomach cancer, colon cancer, larynx cancer, lymphatic system cancer, genitourinary tract cancer, bone cancer, prostate cancer, small-cell lung cancer, glioma cancer, colorectal cancer, kidney cancer, epidermas cancer, liver cancer, esophagus cancer, hematopoietic cancer, lympnoma, myeloma, thyroid follicular cancer; a tumour of mesenchymal origin, for example fibrosarcoma or habdomyosarcoma; a tumour of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; Kaposi's sarcoma, chronic lymphocytic leukaemia, mantle cell lymphoma, large B cell lymphoma.

A "therapeutically effective amount" is intended to mean the amount of the inventive salt that, when administered to a subject in need thereof, is sufficient to effect treatment for disease conditions alleviated by the inhibition of cyclin dependent kinases activity. The amount of a given compound of the invention that will be therapeutically effective will vary depending upon factors such as the disease condition and the severity thereof, the identity of the subject in need thereof, etc., which amount may be routinely determined by artisans of ordinary skill in the art.

The "at least one pharmaceutically acceptable carrier, diluent, vehicle or excipient" can readily be selected by one of ordinary skill in the art and will be determined by the desired mode of administration. Illustrative examples of suitable modes of administration include oral, nasal, parenteral, topical, transdermal, and rectal. The pharmaceutical compositions of this invention may take any pharmaceutical form recognizable to the skilled artisan as being suitable. Suitable pharmaceutical forms include solid, semisolid, liquid, or lyophilized formulations, such as tablets, powders, capsules, suppositories, suspensions, liposomes, and aerosols.

Specific embodiments of the invention will now be demonstrated by reference to the following examples. It should be understood that these examples are disclosed solely by way of illustrating the invention and should not be taken in any way to limit the scope of the present invention.

EXAMPLE 1

Preparation of Compound A1 (i.e., the Compound of Formula (III)

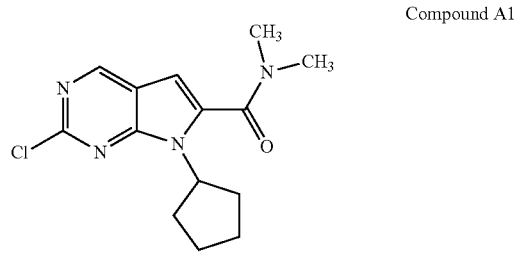 [SMILES: CN(C)C(=O)c1cc2cnc(Cl)nc2n1C1CCCC1]

Compound A1

(i.e., the Compound of Formula (III), 2-chloro-7-cyclopentyl-N,N-dimethyl-7H-pyrrolo[2,3-d]pyrimidine-6-carboxamide) is prepared according to the Synthesis Scheme below.

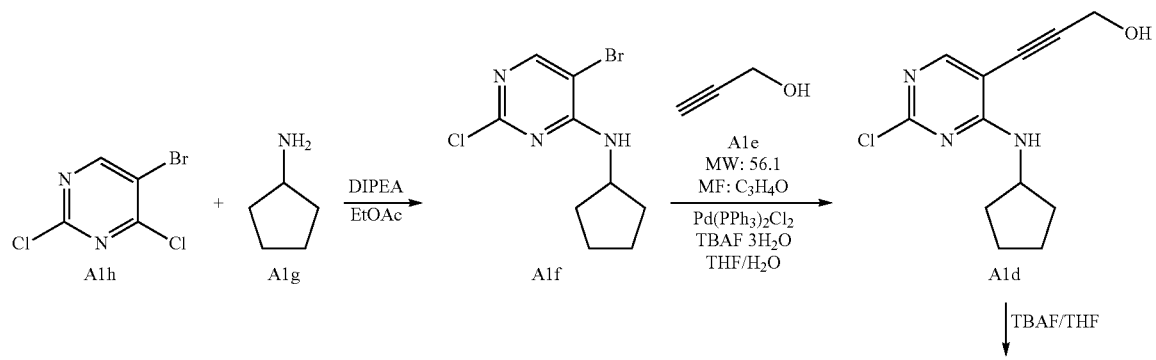

-continued

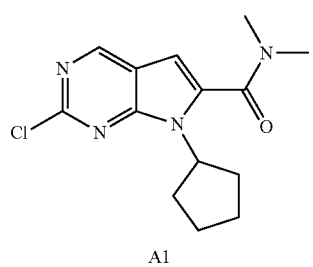 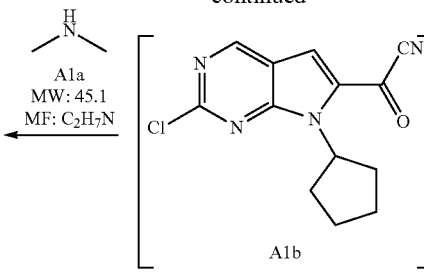 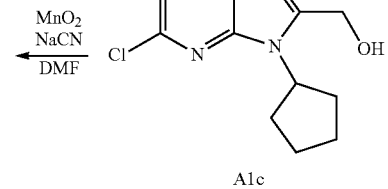

Details of each of the steps is provided below in Steps 1.1-1.4. Step 1.5 is an optional purification step.

1.1
5-Bromo-2-chloro-N-cyclopentylpyrimidin-4-amine (A1f)

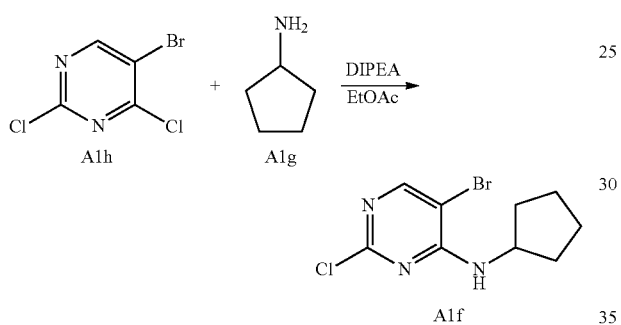

A nitrogen-flushed, suitably equipped 5 L 4-neck round bottom flask is charged with 250 g (1.097 mol, 140.4 mL, 1.0 eq.) of 5-bromo-2,4-dichloropyrimidine (A1h) and 1127 g, (1250 mL) of ethyl acetate. The content is stirred at 20° C. and 283.5 g (2.194 mol, 382.0 mL, 2.0 eq.) of N,N-diisopropylethylamine is added. A solution of 102.8 g (1.207 mol, 119 mL, 1.1 eq.) of cyclopentylamine (A1g) dissolved in 1127 g, (1250 mL) of ethyl acetate is added over 60 min. An 18° C. to 36° C. exotherm is observed. The solution is warmed to 40° C. This temperature is maintained for at least 6 h or until all the starting material A1h, is consumed as determined by HPLC analysis. The resulting slurry is cooled to 25° C. and 500 g (500 mL) of water is added. The content is stirred for 15 min and the phases are allowed to separate. The bottom (aqueous) layer is removed and the organic layer is washed once more with 500 g (500 mL) of water. The sample is stirred for 15 min, and the phases are allowed to separate. The bottom (aqueous) layer is removed. The organic phase is concentrated (atmospheric pressure) to a volume of 1500 mL (batch temp=82° C.). 684 g (1 L) of heptane is added and the concentration is resumed to a volume of 1500 mL (batch temp=85° C.). Again, 684 g (1 L) of heptane is added and the concentration is resumed to a volume of 1500 mL (batch temp=96° C.). The sample is cooled to 50° C. and seeded. The cooling is continued to 4° C. and the temperature is maintained at 4° C. for 1 h. The solids are filtered and the filter cake is washed once with 137 g (200 mL) of cold (4° C.) heptane.

The solids are dried at 50° C. for 16 h, to afford 259.0 g (88.0%, corrected) of Compound A1f as a white, crystalline solid, mp=95-96° C.

1.2 3-[2-Chloro-4-(cyclopentylamino)pyrimidin-5-yl]prop-2-yn-1-ol (A1d

A nitrogen-flushed, suitably equipped 5 L 4-neck round bottom flask is charged with 200 g (0.723 mol, 1.0 eq.) of 5-bromo-2-chloro-N-cyclopentylpyrimidin-4-amine (A1f) and 2303 g, (2600 mL) of tetrahydrofuran. The mixture is stirred, heated to reflux (67° C.) and 200 mL of distillate is collected. The sample is cooled to 25° C. and 52.7 g (0.940 mol, 55.6 mL, 1.3 eq.) of propargyl alcohol (A1e), 570.3 g (1.808 mol, 2.5 eq.) of tetrabutylammonium fluoride trihydrate and 25.4 g (0.036 mol, 0.05 eq.) of bis(triphenylphosphine)palladium (II) dichloride are added. The sample is stirred, heated to reflux (67° C.) and maintained at this temperature for 2 h or until 5-7% of the starting material A1f remains as determined by HPLC analysis. The sample is cooled to 25° C. and concentrated under reduced pressure (100 mbar, 30° C. maximum internal temperature) to a volume of 1150 mL to remove tetrahydrofuran. 541 g, (600 mL) of ethyl acetate is charged. The sample is again concentrated under reduced pressure (100 mbar, 30° C. maximum internal temperature) to a volume of 1150 mL to remove residual tetrahydrofuran. 2706 g (3000 mL) of ethyl acetate and a solution of 63 g of sodium bicarbonate dissolved in 1500 g (1500 mL) of water are added. The sample is stirred at 25° C.

for 10 min and the phases are separated. The organic (top) phase is washed once with 1500 g (1500 mL) of water. The sample is stirred for 10 min and the phases are separated. The organic (top) phase is concentrated under reduced pressure (100 mbar, 30° C. maximum internal temperature) to a volume of 625 mL to remove ethyl acetate. 1582 g (2000 mL) of acetone is added to the concentrate. The sample is stirred, heated to reflux (58° C.) and maintained at this temperature for 30 min. It is then cooled to 40° C. and clarified by filtering through a pad of filter cel. The flask and filter cake are washed twice with 158 g (200 mL, 2×100 mL per wash) of acetone. The sample is concentrated under reduced pressure (100 mbar, 30° C. maximum internal temperature) to a volume of 460 mL. It is then cooled to 4° C. and is hold at this temperature for 1 h. The solids are filtered and the filter cake is washed twice with 158 g (2×100 mL) of cold (4° C.) acetone. The solids are dried at 50° C. for 16 h, to afford 85.6 g (47.4%, corrected) of Compound A1d as a tan, crystalline solid, mp=162-163° C.

1.3 (2-chloro-7-cyclopentyl-7H-pyrrolo[2,3-d]pyrimidin-6-yl)methanol (A1c)

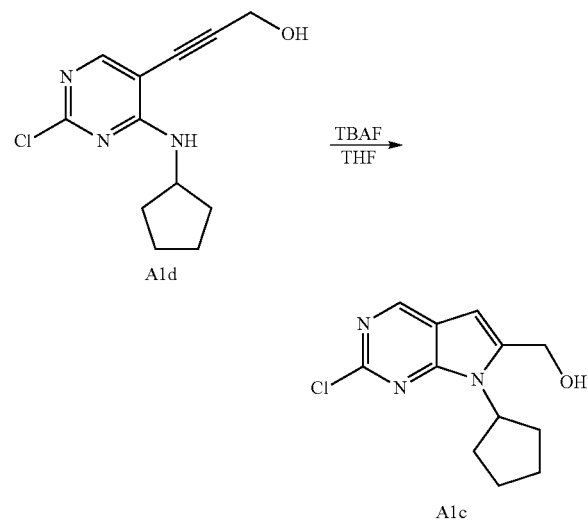 [SMILES: OCC#Cc1cnc(Cl)nc1NC1CCCC1 ; "TBAF" ; OCc1cc2cnc(Cl)nc2n1C1CCCC1 ; "THF"]

A dry nitrogen-flushed 5 L 4-neck round bottom flask is charged with 100 g (Purity: 98%, 0.389 mol 1.0 eq.) of 3-(2-chloro-4-(cyclopentylamino)pyrimidin-5-yl)prop-2-yn-1-ol, (A1d), 880 g (1000 mL) of peroxide free tetrahydrofuran and 753 g, (856 mL) of tetrabutylammonium fluoride, 1.0M solution in THF. The content is stirred at 25° C. for 10 min, and then the solution is warmed to 60° C. This temperature is maintained for 1.5 h until the starting material, A1d, is ≤2.5±0.5% as determined by HPLC analysis. The resulting solution is cooled to below 30±3° C.², and distilled under reduced pressure to remove THF. 79 g (100 mL) of 2-propanol is added. The sample is stirred for 15 min and 1000 g (1000 mL) of water then add slowly over 30 min The sample is stirred at 20±3° C. for 30 min and then filtered. The cake is washed twice with 200 g (2×100 mL) of water. The solids are dried at 50° C. for 16 h to afford Compound A1c as a tan, crystalline solid, mp=174-176° C.

1.4 2-Chloro-7-cyclopentyl-N,N-dimethyl-7H-pyrrolo[2,3-d]pyrimidine-6-carboxamide (A1)

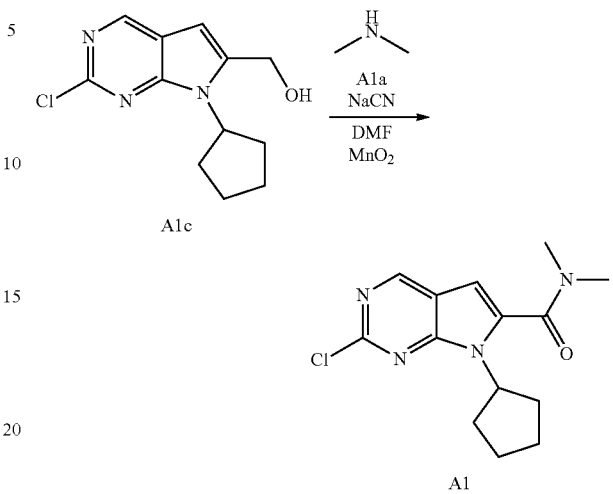

A dry, nitrogen-flushed ACE-100 L Reaction vessel is charged with 97.3 g of sodium cyanide, 2,500 g of (2-chloro-7-cyclopentyl-7H-pyrrolo[2,3-d]pyrimidin-6-yl)methanol, A1c, 16,680 g (19.5 L) of dimethylamine, A1a (2.0M solution in THF), and 28,320 g (30.0 L) of anhydrous N,N-dimethylformamide. The mixture is stirred at 20±3° C. for 15 min 2.06 kg of manganese(IV) oxide is then added. The dark slurry is stirred for 30 min and 12.36 Kg of manganese (IV) oxide is added in three portions ($1^{st}$ portion: 2.06 kg; $2^{nd}$ portion: 4.12 g, and $3^{rd}$ portion: 6.18 kg) every 30 min. After the last portion has been added, the sample is held for 1 h and then 6.18 kg of manganese(IV) oxide is added. The sample is held for 1 h. The reaction mixture is then sampled. The reaction is considered complete if the starting material, A1c is ≤1.0±0.5% as determined by HPLC analysis. The reaction mixture is then filtered through a pad of celite to remove manganese (IV) oxide. The reactor and cake are rinsed with 23 L of ethyl acetate. The filtrate and distil are combined under reduced pressure (45±3° C., 20 mbar) to remove THF, dimethylamine and ethyl acetate. The sample is further distilled under reduced pressure (70±5° C., 5 mbar) to remove DMF. The concentrate is diluted with 35 L of ethyl acetate. The resulting dark solution is washed with aqueous ferrous sulfate solution (1 kg of $FeSO_4 \cdot 7H_2O$ in 14 L of water), 15 L of water and finally 15 L of 10% aqueous NaCl solution. The phases are separated after each wash. The organic phase is distilled (45° C., 50 mbar) to azeotropically remove water. The resulting crude A1 (2,788 g of a dark, thick, semi-solid residue) can be used directly in the next step.

1.5 Procedure: Isolation of pure A1 from crude A1

Optionally the crude A1 from step 1.4 can be purified by either Method 1 or 2 below.

Method-1:

10 g of crude A1 and 9 mL of 1-propanol are warned gently until a homogeneous, dark solution is obtained. The solution is cooled to 25±3° C. and 30 to 40 mL of hexane is slowly added. The sample is seeded and stirred until crystals are observed. An additional 50 to 60 mL of hexane is slowly added. The total volume of hexane added is about 90 mL. The slurry is held at 22±3° C. for 2 h, then cooled to 4° C. and held for an additional 2 h. The solids are filtered. The flask and filter cake are washed with hexane as needed. The filter cake is dried at 50° C., 50 mbar to afford 6.35 g of purified A1 as a light tan, crystalline solid. Recovery: 63.5%.

Method 2:

A solution of 10 g of crude A1 in 10 mL of EtOAc is prepared and loaded onto a 100 g bed of silica gel. The column is eluded with 300 mL of EtOAc/hexane (2/8) and the eluant is disgarded. The column is then elude with 800 mL of EtOAc/hexane (5/5) and the eluant is collected (#2) for isolation of the product. The eluant (#2) is concentrated to thin oil. 100 mL of hexane is slowly added and the sample is stirred at 22±3° C. for 2 h. The sample is cooled to 4° C. and held an additional 2 h. The solids are filtered. The flask and filter cake are washed with hexane as needed. The filter cake is dried at 50° C., 50 mbar to afford 6.05 g of purified A1 as a light tan, crystalline solid. Recovery 60.5%.

EXAMPLE 2

Preparation of Compound A2 (i.e., the Compound of Formula (IV), tert-butyl 4-(6-aminopyridin-3-yl)piperazine-1-carboxylate)

Compound A2

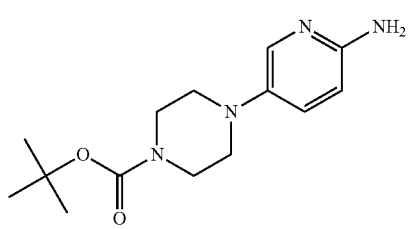

(i.e., the Compound of Formula (IV), tert-butyl 4-(6-aminopyridin-3-yl)piperazine-1-carboxylate) is prepared according to the Synthesis Scheme below.

Details of each of the steps is provided below in Steps 2.1-2.4.

2.1 1-(6-Nitropyridin-3-yl)piperazine hydrochloride (A2b)

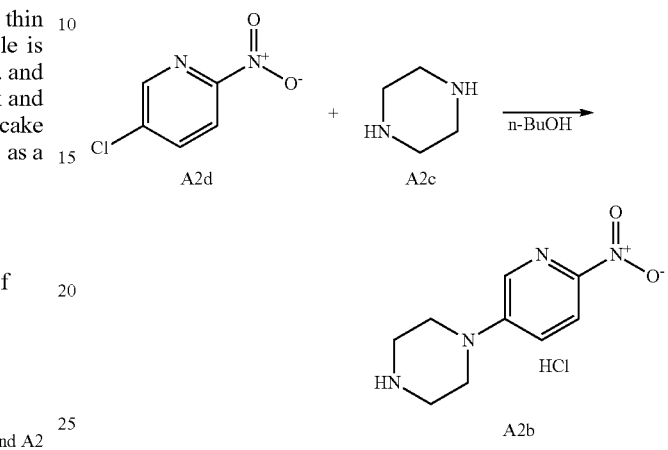

A nitrogen-flushed, suitably equipped 22 L 4-neck round bottom flask is charged with 1392 g (8.78 mol, 1.0 eq.) of 5-chloro-2-nitropyridine (A2d), 1512 g (17.56 mol, 2.0 eq.) of piperazine (A2c) and 11,340 g (14,000 mL) of n-butanol. The resulting suspension is stirred and heated to 95° C. This temperature is maintained for at least 24 h or until the remaining starting material, A2d, is ≥2% (area normalization) as determined by HPLC analysis. The resulting slurry is cooled to 25° C. over 1 h. The solids are filtered through a polypropylene filter pad. The filter cake is washed twice with a total of 2267 g (2×1300 mL) of isopropyl acetate. The solids are Synthesis Scheme dried at 60° C. for 16 h, to afford 1769 g (82.3%, uncorrected) of A2b as a yellow, crystalline solid, mp>230° C. (dec.).

2.2 tert-Butyl 4-(6-Nitropyridin-3-yl)piperazine-1-carboxylate (A2a)

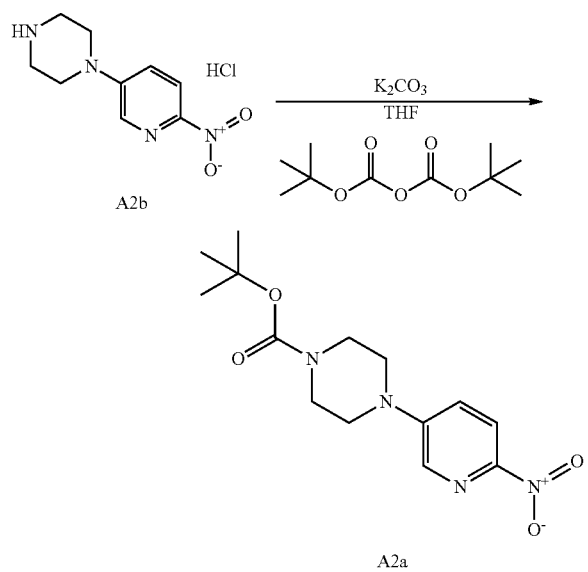 [SMILES: O=[N+]([O-])c1ccc(N2CCNCC2)cn1 ; Cl ; CC(C)(C)OC(=O)OC(=O)OC(C)(C)C ; "K2CO3" ; CC(C)(C)OC(=O)N1CCN(c2ccc([N+](=O)[O-])nc2)CC1 ; "THF"]

A nitrogen-flushed, suitably equipped 22 L 4-neck round bottom flask is charged with 589 g (2.41 mol, 1.0 eq.) of 1-(6-nitropyridin-3-yl)piperazine hydrochloride (A2b). A solution of 630.5 g (2.89 mol, 1.2 eq) of di-tert-butyl dicarbonate in 10,223 g (11,500 mL) of tetrahydrofuran is prepared and charged to the flask. The resulting suspension is stirred and cooled to 8±3° C. A nitrogen-flushed, suitably equipped 5 L 4-neck round bottom flask is charged with 499 g (3.61 mol, 1.5 eq.) of potassium carbonate. 3,600 g (3,600 mL) of water is added to the 5 L flask. After stirring a solution is obtained. This solution is cooled to 25±3° C. and transferred to the reaction mixture over 30 min. A batch temperature≤12±3° C. is maintained throughout the addition. The mixture is warmed to 22±3° C. and held at this temperature for an additional 1 h or until the starting material, A2b, is no longer visible as determined by TLC analysis. The 2-phase mixture is filtered through a 250 g pad of Celite. The filter cake is washed twice with a total of 800 g (2×450 mL) of tetrahydrofuran. The wash is combined with the filtrate. The phases are separated and the aqueous (bottom) phase is disgarded. The filtrate is concentrated under reduced pressure (100 mbar, 40° C. internal MAXIMUM.) to a thick paste.

This entire process are repeated twice more. The concentrates from all three runs are combined in a nitrogen-flushed, suitably equipped 22 L 4-neck round flask. 4,719 g (6,900 mL) of heptane is charged to the concentrated batches. The sample is stirred and concentrated under reduced pressure (100 mbar, 40° C. internal MAXIMUM.) to a thick paste. Again, 3,146 g (4,600 mL) of heptane is charged to the concentrated batch. The resulting suspension is stirred at 37±3° C. for 1 h; cooled to 22±3° C., held for 15 min. The solids are filtered through a polypropylene filter pad and washed twice with 615 g (2×450 mL) of heptane. The solids are dried at 55° C. with a nitrogen sweep[2] for 16 h, to afford 2,088 g (93.8%) of Compound A2a as a yellow, crystalline solid, mp 173-174° C.

2.3 tert-Butyl 4-(6-Aminopyridin-3-yl)piperazine-1-carboxylate (A2)

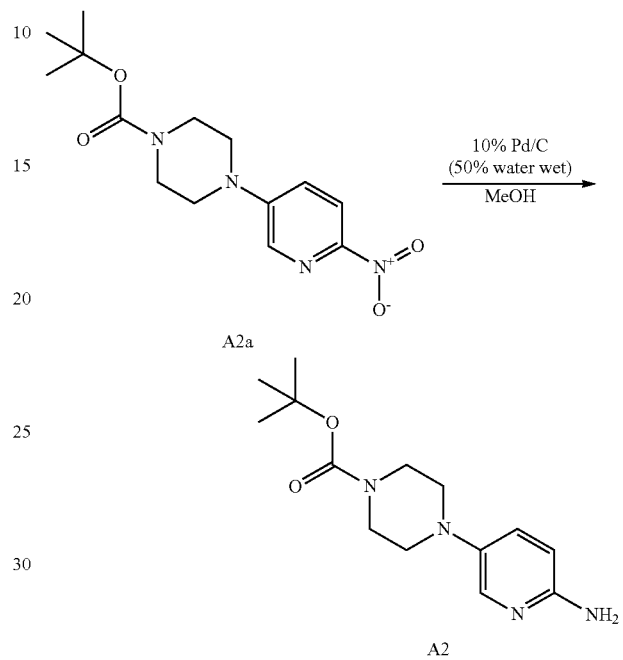

A nitrogen-flushed, 2.5 L heavy-wall Parr bottle (pressure rated to 60 psi) is charged with 68 g (0.22 mol,) of tert-butyl 4-(6-nitropyridin-3-yl)piperazine-1-carboxylate, (A2a), 6.8 g of 10% palladium on carbon, 50% water wet catalyst and 807 g (1020 mL) of methanol. The reaction vessel is inerted three times with nitrogen (ca. 30 psi), evacuating the atmosphere above the reaction mixture each time. The vessel is pressurized twice with hydrogen (ca. 30 psi), evacuating the atmosphere above the reaction mixture each time. The reaction vessel is pressurized to 45 psi with hydrogen. The shaker motor is started. The reaction is exothermic. A temperature rise from 19 to 54° C. over 15 min is observed after which time the hydrogen uptake stops. The mixture is allowed to cool to 30° C. over 1 h at which point the shaker is stopped. The hydrogen atmosphere is replaced with nitrogen as described above (Inert the reaction vessel). The catalyst is removed by filtration through a 10 g pad of filter cel. This entire process is repeated once more, both filtrates are combined and charged to a clean 3 L 4-neck round bottom flask.

2.4 Product Isolation

The filtrates from Step 2.3 is stirred and concentrated under reduced pressure (50 mbar, 40° C. internal MAXIMUM.) to a thick paste. 190 g (250 mL) of tert-butyl methyl ether is charged to the residue. The sample is again stirred and concentrated under reduced pressure (50 mbar, 30° C. internal MAXIMUM.) to a thick paste. 342 g (500 mL) of heptane is charged to the residue and the resulting suspension is stirred for 15 min at 22±3° C. The solids are filtered and the filter cake is washed with 68 g (100 mL) of heptane. Dry the solids at 50° C. for 16 h, to afford 112.3 g (93.4%) of Compound A2 as tan plates, mp 124-126° C.

EXAMPLE 3

Preparation of 7-Cyclopentyl-2-(5-piperazin-1-yl-pyridin-2-ylamino)-7H-pyrrolo[2,3-d]pyrimidine-6-carboxylic acid dimethylamide (i.e., the Compound of Formula (I))

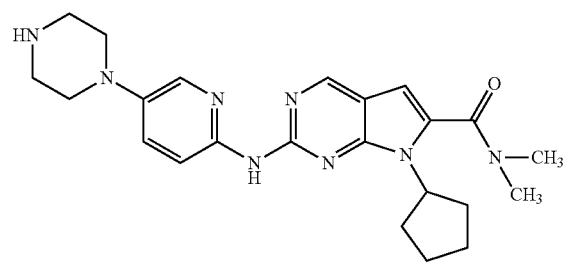

Compound A4

(i.e., the Compound of Formula (I), 7-Cyclopentyl-2-(5-piperazin-1-yl-pyridin-2-ylamino)-7H-pyrrolo[2,3-d]pyrimidine-6-carboxylic acid dimethylamide) is prepared according to the Synthesis Scheme below.

Synthesis Scheme:

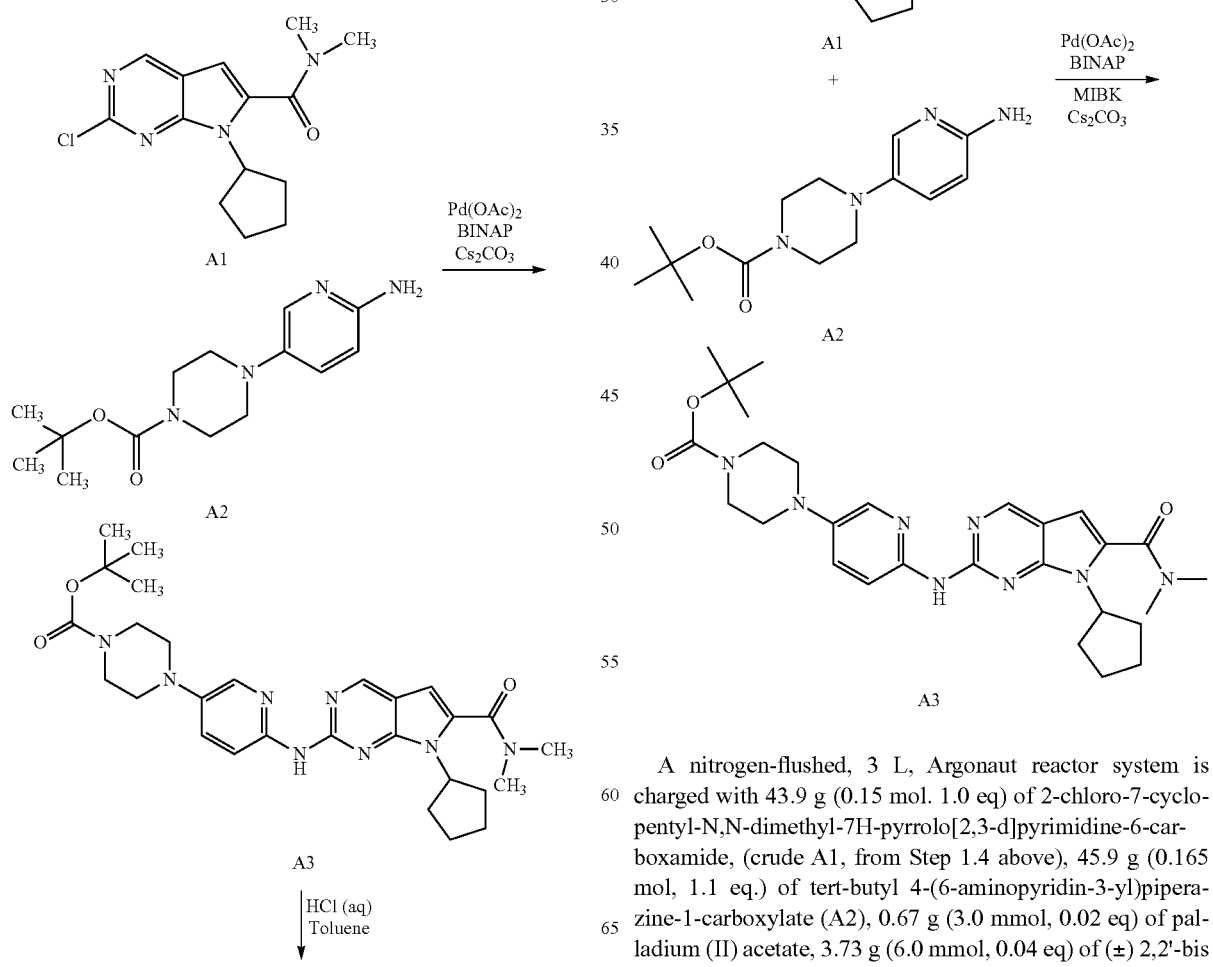

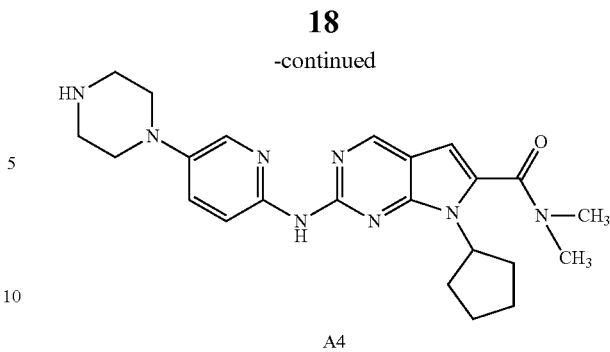

A4

Details of each of the steps is provided below in Steps 3.1-3.2.

3.1 tert-Butyl 4-(6-(7-cyclopentyl-6-(dimethylcarbamoyl)-7H-pyrrolo[2,3-d]pyrimidin-2-ylamino)pyridin-3-yl)piperazine-1-carboxylate (A3)

A nitrogen-flushed, 3 L, Argonaut reactor system is charged with 43.9 g (0.15 mol. 1.0 eq) of 2-chloro-7-cyclopentyl-N,N-dimethyl-7H-pyrrolo[2,3-d]pyrimidine-6-carboxamide, (crude A1, from Step 1.4 above), 45.9 g (0.165 mol, 1.1 eq.) of tert-butyl 4-(6-aminopyridin-3-yl)piperazine-1-carboxylate (A2), 0.67 g (3.0 mmol, 0.02 eq) of palladium (II) acetate, 3.73 g (6.0 mmol, 0.04 eq) of (±) 2,2'-bis(diphenylphosphino)-1,1'-binaphthalene, ±BINAP (2,2'-bis (diphenylphosphino)-1,1'-binaphthyl) and 275 g (344 mL) of 4-methyl-2-pentanone. The resulting suspension is stirred and heated to 40±3° C. 73.3 g (0.225 mol, 1.5 eq) of cesium carbonate is added in 5 to 10 g portions over 15 min. The resulting suspension is stirred and heated to 100±3° C. This temperature is maintained for 3 h or until the remaining starting material, A1, is ≤2% (area normalization) as determined by HPLC analysis. The progress of the reaction is checked using the Process Steering Control. The sample is cooled to 70±3° C. and 344 g (344 mL) of water is added over 5 min. The sample is cooled to 50±3° C. and held at this temperature for 30 min. 353 g (516 mL) of heptane is added over 30 minutes and the sample is stirred for 2 h. The mixture is then cooled to 22±3° C. and held at least 4 h (hold point). The solids are filtered through a polypropylene filter pad. The filter cake is washed with a cold (4° C.) mixture of 24 g (30 mL) of 4-methyl-2-pentanone and 41 g (60 mL) of heptane. The solids are dried at 60° C. until HSGC PSC shows organic solvents to be 1%, to afford 72.6 g of A3 as a tan solid mp 215-217° C. (dec.).

3.2 7-Cyclopentyl-N,N-dimethyl-2-(5-(piperazin-1-yl)pyridin-2-ylamino)-7H-pyrrolo[2,3-d]pyrimidine-6-carboxamide (A4)

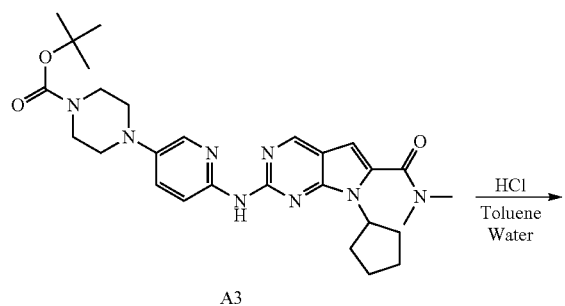

A3

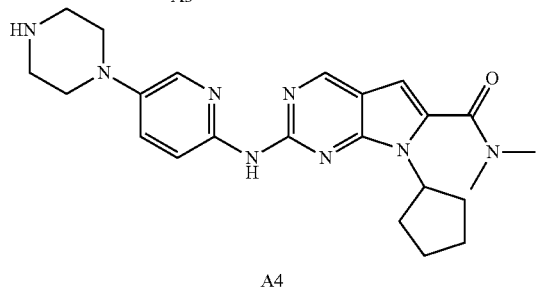

A4

A nitrogen-flushed, 3 L Argonaut reactor system is charged with 67.4 g (0.126 mol, 1.0 eq.) of tert-Butyl 4-(6-(7-cyclopentyl-6-(dimethylcarbamoyl)-7H-pyrrolo[2,3-d]pyrimidin-2-ylaminopyridin-3-yl)piperazine-1-carboxylate (A3) and 329 g (380 mL) of toluene. The suspension is stirred and cooled to 12±3° C. 138 g (126 mL, 6.0 eq) of 6N aqueous hydrochloric acid is added over 30 min maintaining a batch temperature≤15±3° C. The resulting 2-phase solution is warmed to 25±3° C. and held at this temperature for 30 min or until the remaining starting material, A3, is 2% (area normalization) as determined by HPLC analysis. The progress of the reaction is checked using the Process Steering Control. 250 g (250 mL) of 1N hydrochloric acid is added and mixture is stirred for 5 min. The 2-phase reaction mixture is filtered through 25 g of filter cel. The phases are separated. The aqueous phase (containing product) is charged to a 2 L, 4-neck, round bottom flask (equipped as described under Apparatus entry 4) and cooled to 15±3° C. The pH is adjusted to 3.2±0.3 with the slow addition of 62 g (41 mL) of 50% aqueous sodium hydroxide, a batch temperature≤27±3° C. is maintained throughout the addition. 16.4 g of Si-Thiol functionalized silica gel is added. The slurry is stirred for 3 hours at 50±3° C. The resin is filtered off, the flask and filter cake are rinsed with 50 mL of water. The wash is combined with the filtrate. The filtrate is transferred back to the flask and 16.4 g of Si-Thiol functionalized silica gel is added. The slurry is stirred for 3 hours at 50±3° C. The silica gel is filtered off. The flask and filter cake are rinsed with 50 mL of water. The wash is combined with the filtrate. The filtrate is transferred back to the flask and again 16.4 g of Si-Thiol functionalized silica gel is added. The slurry is stirred for 3 hours at 50±3° C. The silica gel is filtered off. The flask and filter cake are rinsed with 50 mL of water. The wash is combined with the filtrate. A nitrogen-flushed, 3 L, Argonaut reactor system is charged with the filtrate and cooled to 15±3° C. The pH is adjusted to 12.5±0.5 with the slow addition of 17 g (18 mL) of 50% aqueous sodium hydroxide to precipitate the product (Batch volume=900 mL, Max Vol). The sample is stirred for at least 6 h at 22±3° C. The solids are filtered through a polypropylene filter pad. The filter cake is washed four times with 340 g (4×85 mL) of water until the pH of the wash is ≤9. The solids are dried at 60° C. for at least 16 h or until the LOD is ≤1% to afford 45.7 g (84.9%, corrected) of compound A4 as a tan solid, mp 194-195° C.

EXAMPLE 4

Preparation of the Succinate salt of 7-Cyclopentyl-2-(5-piperazin-1-yl-pyridin-2-ylamino)-7H-pyrrolo[2,3-d]pyrimidine-6-carboxylic acid dimethylamide (i.e., Compound A6, the Compound of Formula (II))

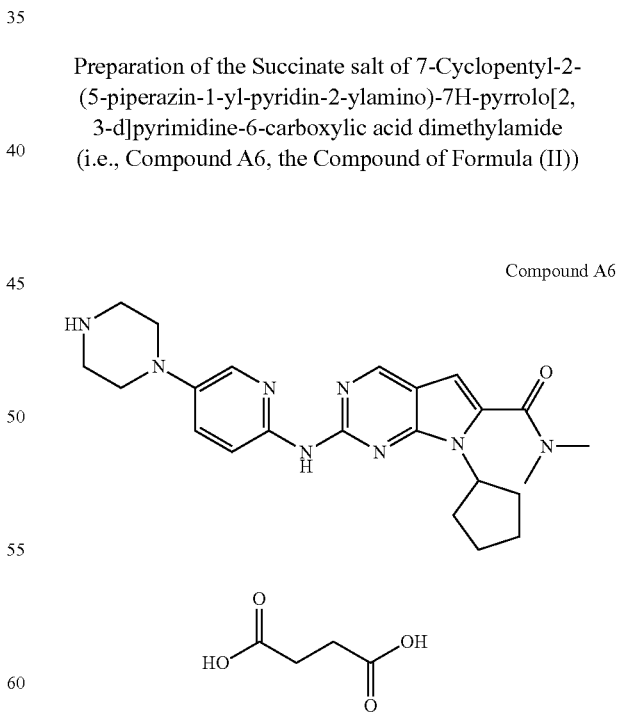

Compound A6

(i.e., the Compound of Formula (II), 7-Cyclopentyl-N,N-dimethyl-2-(5-(piperazin-1-yl)pyridin-2-ylamino)-7H-pyrrolo[2,3-d]pyrimidine-6-carboxamide succinate) is prepared according to the Synthesis Scheme below.

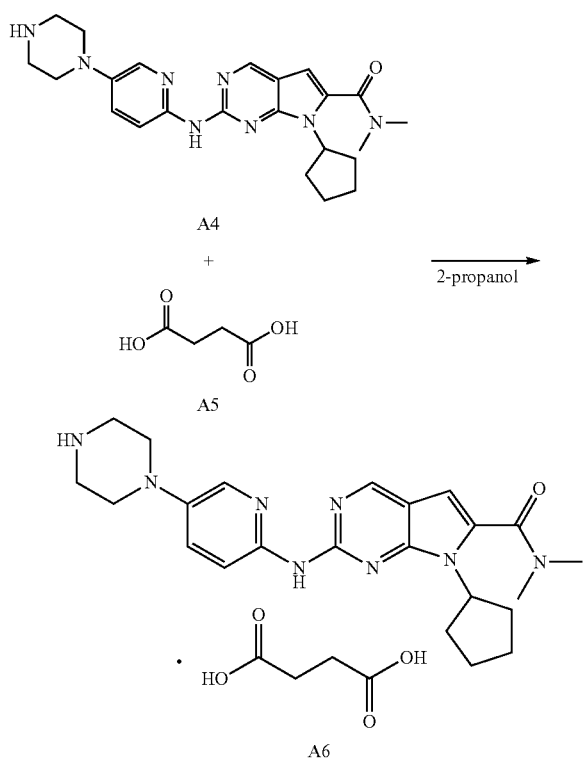

A nitrogen-flushed, 1 L, 4-neck, round bottom flask is charged with 11.16 g (0.0945 mol, 1.05 eq.) of succinic acid (A5), and 245 g (312 mL) of 2-propanol. The suspension is stirred and warmed to 65±3° C. to obtain a clear solution. The solution is filtered while warmed through glass-fiber filter paper. The filtrate is held at 30±3° C. for addition to A4. A nitrogen-flushed 2 L, 4-neck, round bottom flask is charged with 39.11 g (0.09 mol, 1.0 eq) of 7-cyclopentyl-N,N-dimethyl-2-(5-(piperazin-1-yl)pyridin-2-ylamino)-7H-pyrrolo[2,3-d]pyrimidine-6-carboxamide (A4) and 1115 g (1420 mL) of 2-propanol. The resulting suspension is stirred and heated to 80±3° C. to obtain a hazy yellow solution. The solution is cooled to 70±3° C. and filtered through a 25 g pad of Celite. The warm, filtered A4 solution is transferred to a nitrogen-flushed, 3 L, Argonaut reactor system and re-heated to 80±3° C. The succinic acid/2-propanol solution is added over 1 h maintaining 80±3° C. throughout the addition. The batch is seeded after 80% of the succinic acid solution has been added. The sample is stirred at 80±3° C. for 1 h after the addition is completed and cooled to 20±3° C. over 1 h, held 30 minutes and the solids are filtered. The filter cake is washed with 78 g (100 mL) of 2-propanol. The solids are dried at 60° C. for at least 16 h or until the LOD is ≤1% to afford 47.16 g (94.9%, corrected) of Compound A6 as a yellow, crystalline solid, mp 202-203° C.

EXAMPLE 5

Physical Form Characterization of the Compound of Formula (II) Under 90% RH

Figure 2:
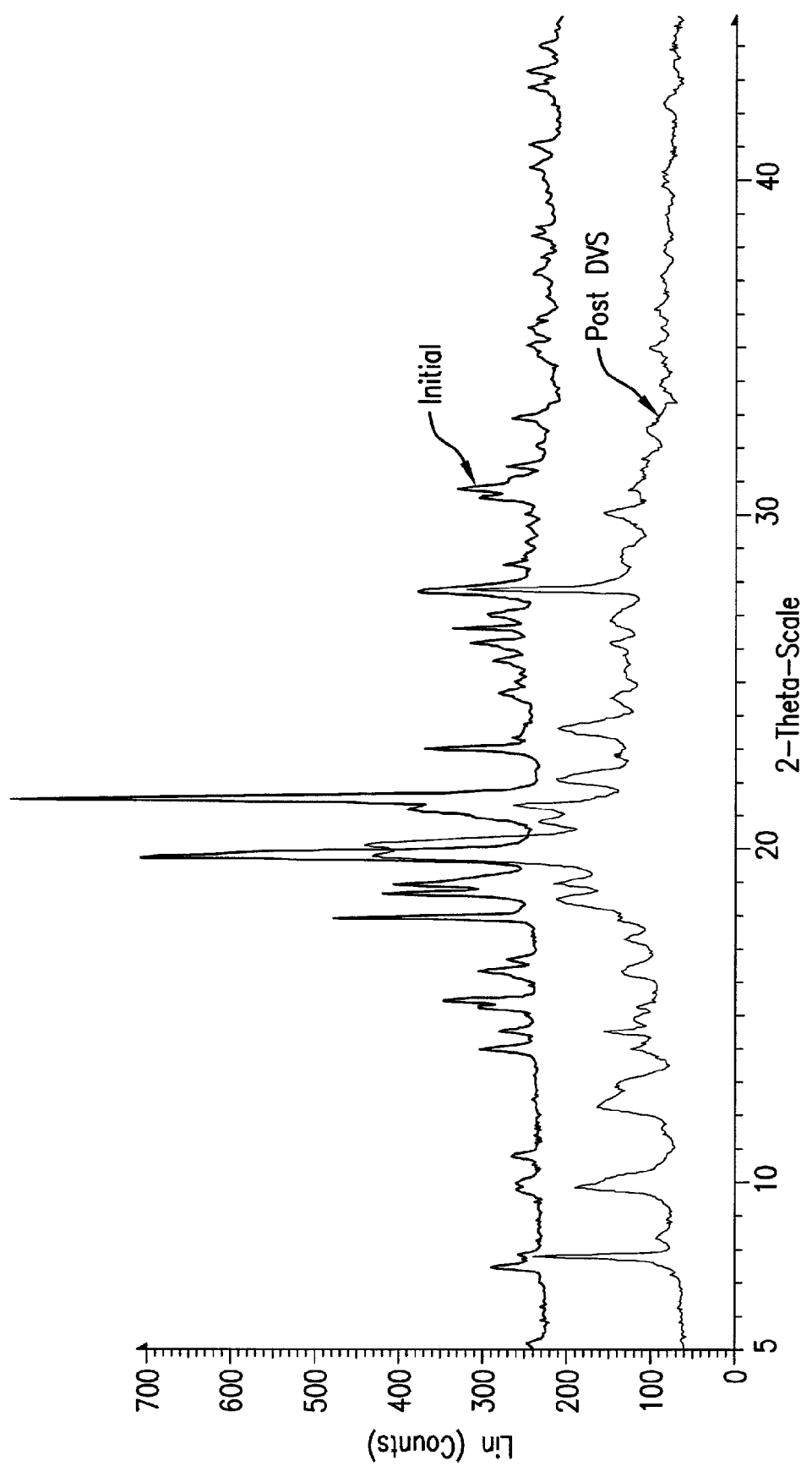
FIG. 2 shows X-ray Powder Diffraction (XRPD) after DVS of Compound of Formula (II) (0-90-0% RH Cycle).
Figure 3:
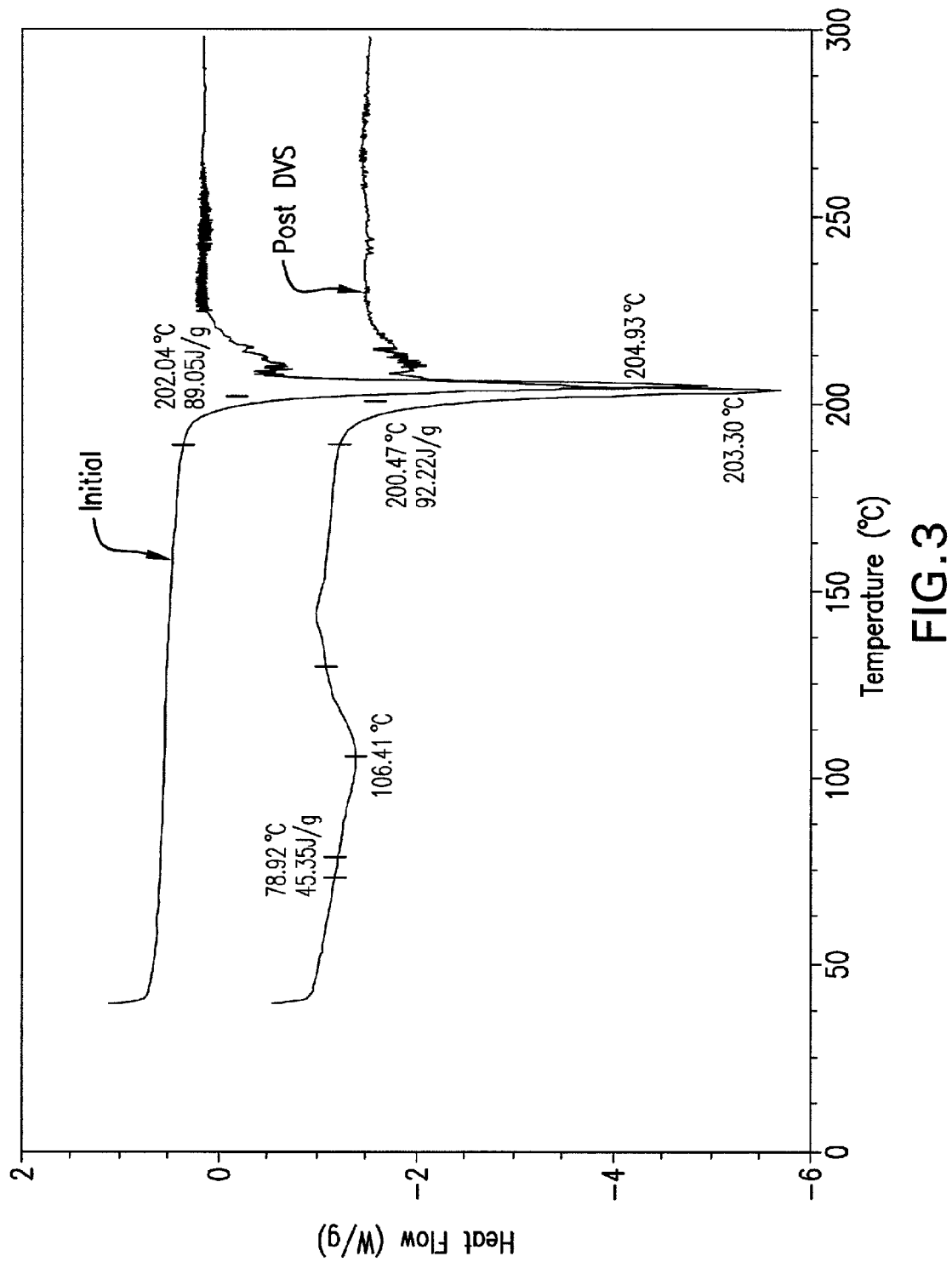
FIG. 3 shows Differential Scanning Calorimetry (DSC) of Compound of Formula (II) after DVS (0-90-0% RH Cycle).
Figure 4:
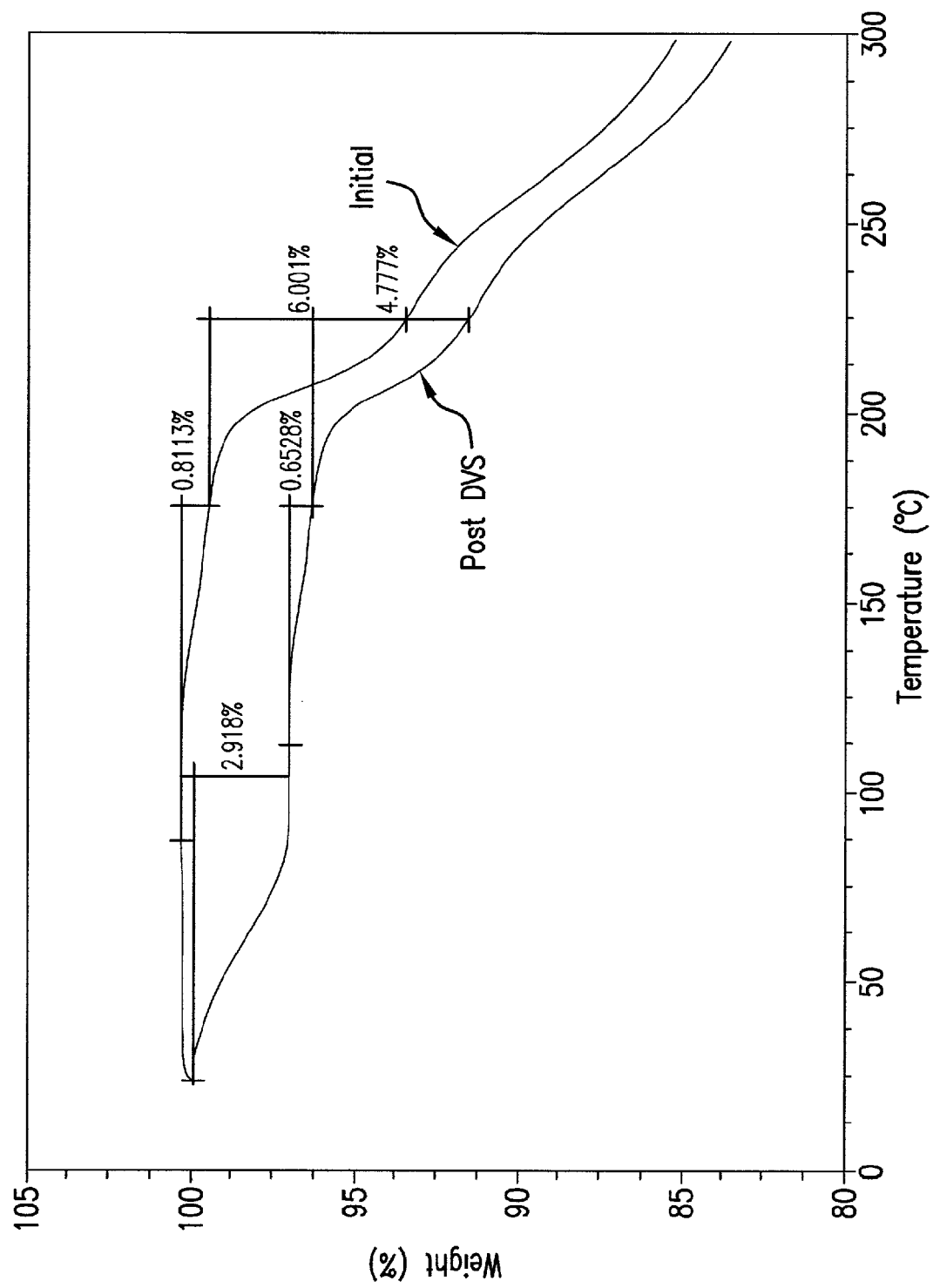
FIG. 4 shows Thermogravimetric Analysis (TGA) of Compound of Formula (II) after DVS (0-90-0% RH Cycle).

To understand its hygroscopic nature, Compound A6 obtained in Example 4 is exposed to two moisture cycle of 0 to 90 to 0% RH. Table 1 and FIG. 1 shows the Compound A6 absorbs up to 2% moisture at 90% RH in each cycle, reflecting slight hygroscopic behavior at high humidity conditions. Also a steep rise in moisture absorption is observed at 90% RH condition in each cycle and difference in sorption and desorption behavior reflects a formation of hydrate form is taking place at 90% RH condition. FIGS. 2, 3 and 4 show change in physical form up on exposure to 90% RH for the compound A6 as a different crystalline form is observed with a endothermic transition which shows a weight loss of 3% around 100° C., both of which conversion to a hydrate form after exposure to 90% RH.

At 90% RH, about 7.35% of the Compound A6 obtained in Example 4 is converted from the non-hydrate form to hydrate form.

EXAMPLE 6

Physical Form Characterization of the Compound of Formula (II) Under 90% RH

Figure 5:
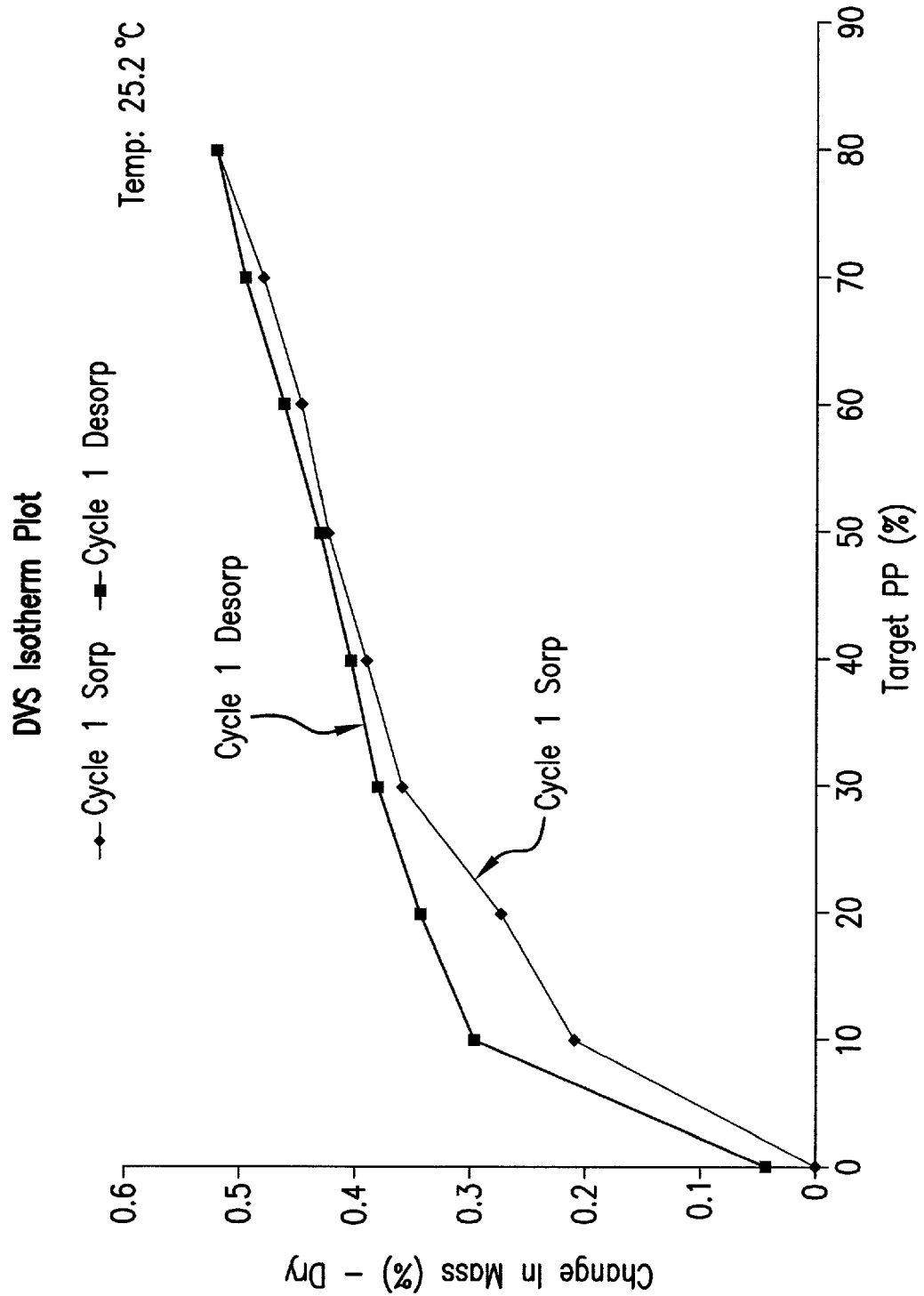
FIG. 5 shows DVS isotherm plot of Compound of Formula (II) (0-80-0% RH Cycle).
Figure 6:
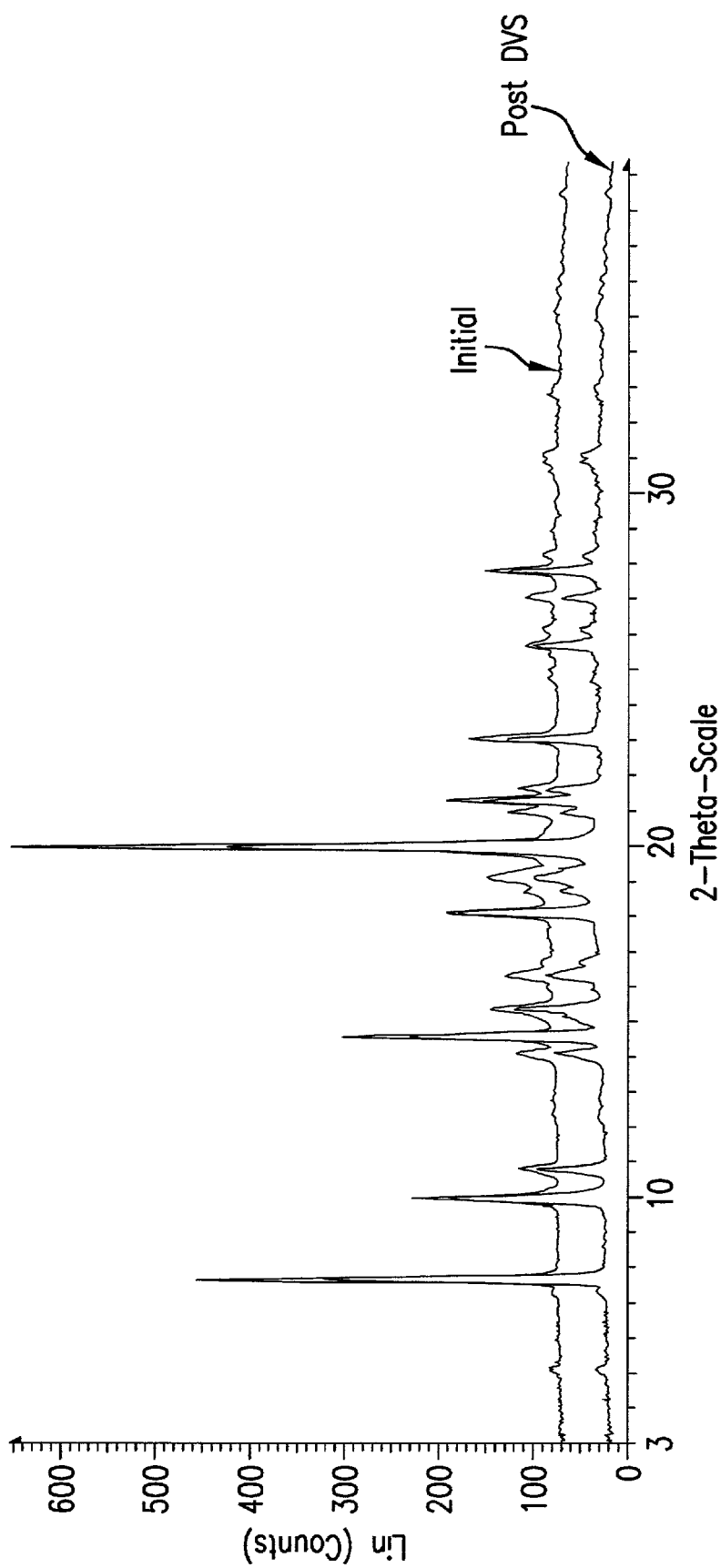
FIG. 6 shows XRPD after DVS of Compound of Formula (II) (0-80-0% RH Cycle).

To confirm that the form change observed under 90% RH is not taking place at 80% RH, compound A6 obtained in Example 4 is exposed to a moisture cycle of 0 to 80 to 0% RH. Table 2 and FIG. 5 shows Compound A6 absorbs up to 0.5% moisture at 80% RH reflecting nearly non-hygroscopic behavior at 80° C. FIGS. 5 and 6 show stability of the physical form of Compound of Formula (II) up on exposure to 80% RH which is reflective of non-hydrate form. Since for stability of drug substance and drug product a physical form stability at 75% RH is desirable, Compound of Formula (II) (non-hydrate) is suitable for development.

At 80% RH, only about 0.52% of the Compound A6 obtained in Example 4 is converted from the non-hydrate form to hydrate form.

EXAMPLE 7

Solubility

The solubility of the non-hydrate form in water is about 30 mg/ml. In contrast, the solubility of the hydrate form is significantly lower and is less than 0.5 mg/ml.

TABLE 1

Isotherm table of Compound of Formula (II) (0-90-0% RH Cycle)

| | Target RH (%) | Sorption | Change In Mass (%) − ref Desorption | Hysteresis |
|---|---|---|---|---|
| Cycle 1 | 0.0 | 0.002 | 0.348 | |
| | 10.0 | 0.110 | 1.721 | 1.611 |
| | 20.0 | 0.156 | 1.977 | 1.821 |
| | 30.0 | 0.201 | 2.140 | 1.939 |
| | 40.0 | 0.222 | 2.254 | 2.032 |
| | 50.0 | 0.242 | 2.332 | 2.090 |
| | 60.0 | 0.261 | 2.403 | 2.142 |
| | 70.0 | 0.250 | 2.466 | 2.216 |
| | 80.0 | 0.251 | 2.514 | 2.262 |
| | 90.0 | 2.503 | 2.503 | |
| Cycle 2 | 0.0 | 0.348 | 0.441 | |
| | 10.0 | 1.617 | 2.634 | 1.017 |
| | 20.0 | 1.904 | 3.004 | 1.100 |
| | 30.0 | 2.078 | 3.216 | 1.138 |
| | 40.0 | 2.207 | 3.378 | 1.170 |
| | 50.0 | 2.303 | 3.492 | 1.188 |
| | 60.0 | 2.377 | 3.593 | 1.215 |
| | 70.0 | 2.426 | 3.675 | 1.249 |
| | 80.0 | 2.474 | 3.750 | 1.277 |
| | 90.0 | 3.808 | 3.808 | |

TABLE 2

Isotherm table of Compound of Formula (II) (0-80-0% RH Cycle)

| | Target RH (%) | Sorption | Change In Mass (%) Desorption | Hysteresis |
|---|---|---|---|---|
| Cycle 1 | 0.0 | 0.0019 | 0.0434 | |
| | 10.0 | 0.2087 | 0.2958 | 0.0871 |
| | 20.0 | 0.2728 | 0.3436 | 0.0708 |
| | 30.0 | 0.3597 | 0.3806 | 0.0209 |
| | 40.0 | 0.3904 | 0.4037 | 0.0133 |
| | 50.0 | 0.4237 | 0.4311 | 0.0074 |
| | 60.0 | 0.4474 | 0.4614 | 0.0140 |
| | 70.0 | 0.4793 | 0.4952 | 0.0159 |
| | 80.0 | 0.5200 | 0.5200 | |

What is claimed is:

1. Succinate salt of 7-Cyclopentyl-2-(5-piperazin-1-yl-pyridin-2-ylamino)-7H-pyrrolo[2,3-d]pyrimidine-6-carboxylic acid dimethylamide characterized by the initial X-ray Powder Diffraction (XRPD) illustrated in FIG. 2.

2. Succinate salt of 7-Cyclopentyl-2-(5-piperazin-1-yl-pyridin-2-ylamino)-7H-pyrrolo[2,3-d]pyrimidine-6-carboxylic acid dimethylamide characterized by the post-DVS X-ray Powder Diffraction (XRPD) illustrated in FIG. 2.

3. Succinate salt of 7-Cyclopentyl-2-(5-piperazin-1-yl-pyridin-2-ylamino)-7H-pyrrolo[2,3-d]pyrimidine-6-carboxylic acid dimethylamide characterized by the initial Differential Scanning Calorimetry (DSC) illustrated in FIG. 3.

4. Succinate salt of 7-Cyclopentyl-2-(5-piperazin-1-yl-pyridin-2-ylamino)-7H-pyrrolo[2,3-d]pyrimidine-6-carboxylic acid dimethylamide characterized by the post-DVS Differential Scanning Calorimetry (DSC) illustrated in FIG. 3.

5. Succinate salt of 7-Cyclopentyl-2-(5-piperazin-1-yl-pyridin-2-ylamino)-7H-pyrrolo[2,3-d]pyrimidine-6-carboxylic acid dimethylamide characterized by the initial Thermogravimetric Analysis (TGA) illustrated in FIG. 4.

6. Succinate salt of 7-Cyclopentyl-2-(5-piperazin-1-yl-pyridin-2-ylamino)-7H-pyrrolo[2,3-d]pyrimidine-6-carboxylic acid dimethylamide characterized by the post-DVS Thermogravimetric Analysis (TGA) illustrated in FIG. 4.

7. Succinate salt of 7-Cyclopentyl-2-(5-piperazin-1-yl-pyridin-2-ylamino)-7H-pyrrolo[2,3-d]pyrimidine-6-carboxylic acid dimethylamide characterized by the initial X-ray Powder Diffraction (XRPD) illustrated in FIG. 6.

8. Succinate salt of 7-Cyclopentyl-2-(5-piperazin-1-yl-pyridin-2-ylamino)-7H-pyrrolo[2,3-d]pyrimidine-6-carboxylic acid dimethylamide characterized by the post-DVS X-ray Powder Diffraction (XRPD) illustrated in FIG. 6.

9. A pharmaceutical composition comprising:
  (a) a therapeutically effective amount of a salt according to any of claims 1-8; and
  (b) at least one pharmaceutically acceptable carrier, diluent, vehicle or excipient.

* * * * *